United States Patent
Imhoff et al.

(10) Patent No.: US 10,376,219 B2
(45) Date of Patent: Aug. 13, 2019

(54) MONITORING DEVICE FOR MONITORING THE STATE OF THE CIRCULATION OF A PATIENT AND COMPUTER PROGRAM PRODUCT FOR THIS MONITORING

(71) Applicant: Drägerwerk AG & Co. KGaA, Lübeck (DE)

(72) Inventors: Michael Imhoff, Lübeck (DE); Ernst-Wilhelm Schubert, Lübeck (DE); Doreen Werner, Hamburg (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 504 days.

(21) Appl. No.: 15/032,436

(22) PCT Filed: Oct. 29, 2014

(86) PCT No.: PCT/EP2014/002902
§ 371 (c)(1),
(2) Date: Apr. 27, 2016

(87) PCT Pub. No.: WO2015/062720
PCT Pub. Date: May 7, 2015

(65) Prior Publication Data
US 2016/0270734 A1    Sep. 22, 2016

(30) Foreign Application Priority Data
Nov. 2, 2013   (DE) .................. 10 2013 018 366

(51) Int. Cl.
*A61B 5/02*    (2006.01)
*A61B 5/00*    (2006.01)
(Continued)

(52) U.S. Cl.
CPC .............. *A61B 5/7217* (2013.01); *A61B 5/02* (2013.01); *A61B 5/021* (2013.01); *A61B 5/029* (2013.01);
(Continued)

(58) Field of Classification Search
None
See application file for complete search history.

(56) References Cited

U.S. PATENT DOCUMENTS 5,181,517 A *   1/1993   Hickey ................ A61B 5/0215
                                                   600/486
2011/0087116 A1*  4/2011  Parkin ................ G06F 19/3418
                                                   600/485

FOREIGN PATENT DOCUMENTS

DE         102 59 780 A1     7/2003
DE      10 2004 024 334 A1   12/2005
(Continued)

OTHER PUBLICATIONS

Francois Feihl et al: "Interactions between respiration and systemic hemodynamics. Part I: basic concepts", Intensive Care Medicine. Springer, Berlin, DE. vol. 35. No. 1. Sep. 30, 2008 (Sep. 30, 2008). pp. 45-54, XP019699333. ISSN: 1432-1238 A p. 49. col. 2, paragraph 4-paragraph 5; figure 4.
(Continued)

*Primary Examiner* — Michael R Bloch
(74) *Attorney, Agent, or Firm* — McGlew and Tuttle, P.C.

(57) ABSTRACT

A monitoring device for the circulation of a patient includes sensors for recording data, an input unit for inputting patient specific data and a connected a data recording and analysis device configured to determine the right atrial pressure (RAP), the mean arterial pressure (MAP) and the cardiac output (CO) and to determine the mean systemic filling pressure (Pms) and to determine the cardiac efficiency (Eh) therefrom. A device records a pressure value (Pps,char)
(Continued)

characterizing the pressure assistance during positive-pressure ventilation. The data recording and analysis device is configured to determine a pressure-corrected mean systemic filling pressure ($Pms_p$) and a pressure-corrected cardiac efficiency ($Eh_p$) by the difference from the right atrial pressure (RAP) and the pressure value (Pps,char) characteristic of the pressure assistance being used instead of the right atrial pressure (RAP). A display device displays the pressure-corrected mean systemic filling pressure ($Pms_p$) and the pressure-corrected cardiac efficiency ($Eh_p$).

11 Claims, 2 Drawing Sheets

(51) Int. Cl.
  *A61B 5/021*  (2006.01)
  *A61B 5/029*  (2006.01)
  *A61M 16/00*  (2006.01)

(52) U.S. Cl.
  CPC ............ *A61B 5/7278* (2013.01); *A61B 5/742* (2013.01); *A61M 16/0057* (2013.01); *A61M 2016/0027* (2013.01)

(56) References Cited

FOREIGN PATENT DOCUMENTS

| | | |
|---|---|---|
| EP | 1 236 435 B1 | 5/2004 |
| WO | 2009/094700 A1 | 8/2009 |

OTHER PUBLICATIONS

William Geoffrey Parkin et al: "Therapeutic control of the circulation". Journal of Clinical Monitoring and Computing, Kluwer Academic Publishers, DO. vol. 22. No. 6. Nov. 12, 2008 (Nov. 12, 2008), pp. 391-400. XP019680686, ISSN: 1573-2614 cited in the application the whole document.

* cited by examiner

MONITORING DEVICE FOR MONITORING THE STATE OF THE CIRCULATION OF A PATIENT AND COMPUTER PROGRAM PRODUCT FOR THIS MONITORING

CROSS REFERENCE TO RELATED APPLICATIONS

This application is a United States National Phase Application of International Application PCT/EP2014/002902 filed Oct. 29, 2014 and claims the benefit of priority under 35 U.S.C. § 119 of German Patent Application 10 2013 018 366.9 filed Nov. 2, 2013 the entire contents of which are incorporated herein by reference.

FIELD OF THE INVENTION

The present invention pertains to a monitoring device for monitoring the state of the circulation of a patient with sensors for recording data characterizing the current state of circulation of the patient, an input unit for inputting the person-specific data of the patient, a data recording and analysis device connected to the sensors and the input unit, which is set up to determine the right atrial pressure (RAP), the mean arterial pressure (MAP) and the cardiac output (CO) from the data characterizing the current state of circulation of the patient and to determine the mean systemic filling pressure (Pms) from the right atrial pressure, mean arterial pressure and cardiac output and to determine the cardiac efficiency (Eh) from the mean systemic filling pressure and from the right atrial pressure (RAP) by means of linear combination with predetermined factors and with factors dependent on the person-specific data and to display the currently determined mean systemic filling pressure (Pms) and the current cardiac efficiency (Eh) as a current state in a system of coordinates defined by the cardiac efficiency and the mean systemic filling pressure on a display device.

BACKGROUND OF THE INVENTION

Such a monitoring device for monitoring and displaying the state of the circulation of a patient is well known from WO 2009/094700 A1. The monitoring of the circulatory function of patients is a central task in intensive care. The monitoring involves the recording of various relevant parameters with sensors in order to derive variables therefrom such as various blood pressure values, blood volume pulses, cardiac output, heart rate, oxygen concentrations, etc. Physicians or medical staff then have to get an idea from these variables of whether the state of the circulation is within a physiologically normal range or whether the circulation is in a critical state with possible malfunctions such that countermeasures shall be taken. A countermeasure may be the administration of additional volumes, e.g., infusion of saline solution, or the administration of various drugs, e.g., of vasoconstricting or vasodilating drugs, or of drugs which have an effect on the activity of the heart. The physician or the medical staff must decide which of the measures are to be taken and in which direction on the basis of a larger number of variables related to the state of the circulation because of predefined strategies and empirical values.

These variables related to state of the circulation can only be interpreted with difficulty in their entirety and in their interaction such that the decision on taking therapeutic countermeasures and the type of therapeutic countermeasures is a complicated problem for the medical staff. For this reason, approaches have already been provided to derive variables from the measured variables of the circulatory function and to display them on a display device, which makes the state of the circulation intuitively more easily recordable. Among other things, it is suggested in the above-mentioned publication WO 2009/094700 to determine the mean systemic filling pressure Pms and the cardiac efficiency Eh as derived variables and display them in a system of coordinates with the mean systemic filling pressure and the cardiac efficiency as axes of coordinates. The system of coordinates does not have to be a Cartesian system in this case, but rather may also be implemented by two parallel, adjacent or otherwise shown axes of coordinates, at which the current values of both variables are shown.

In the cited publication, the mean systemic filling pressure Pms is derived by the following equation:

$$Pms = a \cdot RAP + b \cdot MAP + c \cdot CO \quad [1]$$

in which a and b are predetermined factors and c is a factor, which depends on person-specific data (e.g., age, height, gender) in a predetermined manner.

In this case, the variable RAP is the right atrial pressure, MAP is the arterial mean pressure and CO is the cardiac output, a and b are predetermined, person-independent factors, and factor c is determined by a predetermined dependence from person-specific data (e.g., age, height).

The cardiac efficiency is derived by the following equation:

$$Eh = \frac{Pms - RAP}{Pms} = \frac{a \cdot RAP + b \cdot MAP + c \cdot CO - RAP}{a \cdot RAP + b \cdot MAP + c \cdot CO} \quad [2]$$

If the heart is working too weakly, the RAP value increases, which leads to a decrease in the cardiac efficiency Eh. If the heart stops beating, all pressures are essentially equal to the mean systemic filling pressure Pms such that the cardiac efficiency Eh drops essentially to 0. Further connections and background are described in the article "*Therapeutic Control of the Circulation*" by W. G. Parkin et al., *Journal of Clinical Monitoring and Computing* 2008, 22:391-400.

It is also possible in this connection to display the state values of the pair of values Pms and Eh at consecutive points in time, e.g., as a sequence of points in a system of coordinates so that the course of development of the state of the circulation is visible.

An artificial ventilation with positive-pressure ventilation must often also be carried out in patients in intensive care units. It has been found that the monitoring of the state of the circulation described in the introduction with determination of the mean systemic filling pressure and the cardiac efficiency and the display thereof does not lead to satisfactory and reproducible results in patients with positive-pressure ventilation.

SUMMARY OF THE INVENTION

An object of the present invention is to create a monitoring device for monitoring the state of the circulation, with which consistent and reproducible results for the considered state variables of the circulation can also be achieved in positive-pressure-ventilated patients. Further, a computer program product shall be indicated which makes possible a consistent and reproducible determination of the state variables, mean systemic filling pressure Pms and cardiac efficiency Eh, on a computer providing processing on a data recording and analysis device.

A device for recording a pressure value, which characterizes the pressure assistance during the positive-pressure ventilation, is present in the monitoring device according to the present invention. This pressure value characterizing the pressure assistance during positive-pressure ventilation is abbreviated below as Pps,char. This characteristic pressure value shall be an indicator of the mean pressure assistance and may be a measured pressure value or a pressure value received by a ventilator, set thereon or derived therefrom. The data recording and analysis device is configured to record the characteristic pressure value and to determine a pressure-corrected mean systemic filling pressure ($Pms_p$) and a pressure-corrected cardiac efficiency ($Eh_p$) by using the difference from the right atrial pressure (RAP) and the pressure value characteristic of the pressure assistance Pps,char instead of the right atrial pressure (RAP) in the equations for the determination thereof. This pressure-corrected mean systemic filling pressure $Pms_p$ and the pressure-corrected cardiac efficiency $Eh_p$ are displayed by the data recording and analysis device as a current state in the system of coordinates on the display device.

It has been found that a more accurate determination of the actual state variables in the circulatory system is possible by including the pressure conditions in the respiratory system. For this purpose, the pressure value characterizing the pressure assistance shall be subtracted from the recorded right atrial pressure RAP, since the recorded right atrial pressure RAP in the circulatory system would otherwise be assumed to be too high. It has been shown that the simple subtraction of the right atrial pressure RAP that was recorded by sensors minus the pressure characterizing the pressure assistance leads to a pressure-corrected right atrial pressure, which corresponds much better to the actual right atrial pressure without positive-pressure ventilation.

In a preferred embodiment, provisions are made for the data recording and analysis device to be set up to determine the pressure-corrected mean systemic filling pressure ($Pms_p$) on the basis of the following equation:

$$Pms_p = a \cdot (RAP - 0.76 \cdot Pps,char) + b \cdot MAP + c \cdot CO \qquad [3]$$

in which:
RAP is the right atrial pressure (mmHg)
MAP is the mean arterial pressure (mmHg)
CO is the cardiac output (L/min)
Pps,char is the pressure characterizing the pressure assistance (mbar)
a is the predetermined factor (dimensionless)
b is the predetermined factor (dimensionless)
c is the person-specific factor (dyn·sec·cm$^{-5}$·m$^2$).

In the given equation, the characteristic pressure Pps,char is subtracted with a factor of 0.76 since the pressure values in the circulatory system traditionally are given in the unit mmHg, but the pressure in the respiratory system as Pps,char is given in mbar. Due to the factor of 0.76, the different units are balanced such that the simple difference from RAP and Pps,char is actually obtained if both pressures RAP and Pps,char would be obtained in the same unit. It has been shown that the complete subtraction of the pressure Pps,char from the right atrial pressure RAP leads to the best results.

In an advantageous embodiment, provisions are made for the data recording and analysis unit to be set up to determine the pressure-corrected cardiac efficiency ($Eh_p$) according to the following equation:

$$Eh_p = \frac{[a \cdot (RAP - 0.76 \cdot Pps,char) + b \cdot MAP + c \cdot CO] - [RAP - 0.76 \cdot Pps,char]}{a \cdot (RAP - 0.76 \cdot Pps,char) + b \cdot MAP + c \cdot CO} \qquad [4]$$

with the meanings of the variables given in the previous formula.

The just indicated formula corresponds to the formula already given above $$Eh = \frac{Pms - RAP}{Pms}$$

in which the right atrial pressure RAP is continuously replaced (even at the point, at which it occurs in Pms) with a pressure-corrected value (RAP−0.76" Pps,char).

In the preferred embodiment, the device for recording the pressure value characterizing the pressure assistance is configured to record the positive end-expiratory pressure PEEP as this characterizing pressure value Pps,char. The data recording and analysis device is then set up to use the difference from the right atrial pressure RAP and the positive end-expiratory pressure PEEP in each case rather than the right atrial pressure RAP determined by sensors in the determination of the pressure-corrected mean systemic filling pressure ($Pms_p$) and in the determination of the pressure-corrected cardiac efficiency ($Eh_p$), and especially to insert the variable PEEP for Pps,char in the above-mentioned equations for $Pms_p$ and $Eh_p$. The positive end-expiratory pressure (PEEP) is a pressure value advantageously characterizing the pressure assistance since it reflects the mean increase in the pressure level due to the positive-pressure ventilation and thus is a good indicator of the pressure value in order to reduce the recorded right atrial pressure RAP in the circulatory system in order to have a corrected right atrial pressure enter into the determinations of $Pms_p$ and $Eh_p$, which rather reflects the actual state of circulation without positive-pressure ventilation.

According to an advantageous embodiment, provisions are made for the data recording and analysis device to be set up to store the states of pressure-corrected mean systemic filling pressure ($Pms_p$) and pressure-corrected cardiac efficiency ($Eh_p$) as a function of time and to display the current state from the current pressure-corrected mean systemic filling pressure ($Pms_p$) and pressure-corrected cardiac efficiency ($Eh_p$) together with the stored states at past points in time in the system of coordinates in order to make the course of development of the state visible. In this way, it is possible for the staff to monitor in an intuitively easily recordable manner whether countermeasures possibly taken have led to an improvement in the state of the circulatory system. In particular, provisions may advantageously be made in this case for the data recording and analysis device to be set up to display the course of development as a state curve or trajectory ($Pms_p(t)$, $Eh_p(t)$) with a time stamp in the system of coordinates. The time stamp may occur, for example, along the trajectory by indicating times along the curve.

According to another aspect, the present invention is directed at a computer program product which is configured to control the data recording and analysis device, which comprises a computer. The computer program product is run on the data recording and analysis device such that the data recording and analysis device performs the above-described procedures of the monitoring device as modes of operation of the data recording and analysis device.

The present invention is explained below on the basis of exemplary embodiments in connection with the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

A male patient with the following data is considered as the first example:
Patient: Male, 55 years old, 178 cm, 76 kg (normal weight), acute lung failure after hemorrhage;
cardiac index 5.0 L/min./m2, heart rate 97 per min., blood pressure 128/61 mmHg (MAP 81 mmHg), RAP 15 mmHg;
controlled ventilation with a positive end-expiratory pressure PEEP of 15 mbar.

Thus, the following values were obtained for the state variables by deriving the mean systemic filling pressure Pms and the cardiac efficiency Eh without pressure correction, i.e., by using the formulas [1] and [2]:
Pms=26.01 (clinical evaluation: too high)
Eh=0.35 (clinical evaluation: low).

The pressure-corrected mean systemic filling pressure $Pms_p$ was subsequently determined with the formula [3] and the pressure-corrected cardiac efficiency $Eh_p$ was determined with the equation [4], which leads to the following values for the pressure-corrected state variables:
$Pms_p$=15.07 (clinical evaluation: too low)
$Eh_p$=0.63 (clinical evaluation: good).

Figure 1:
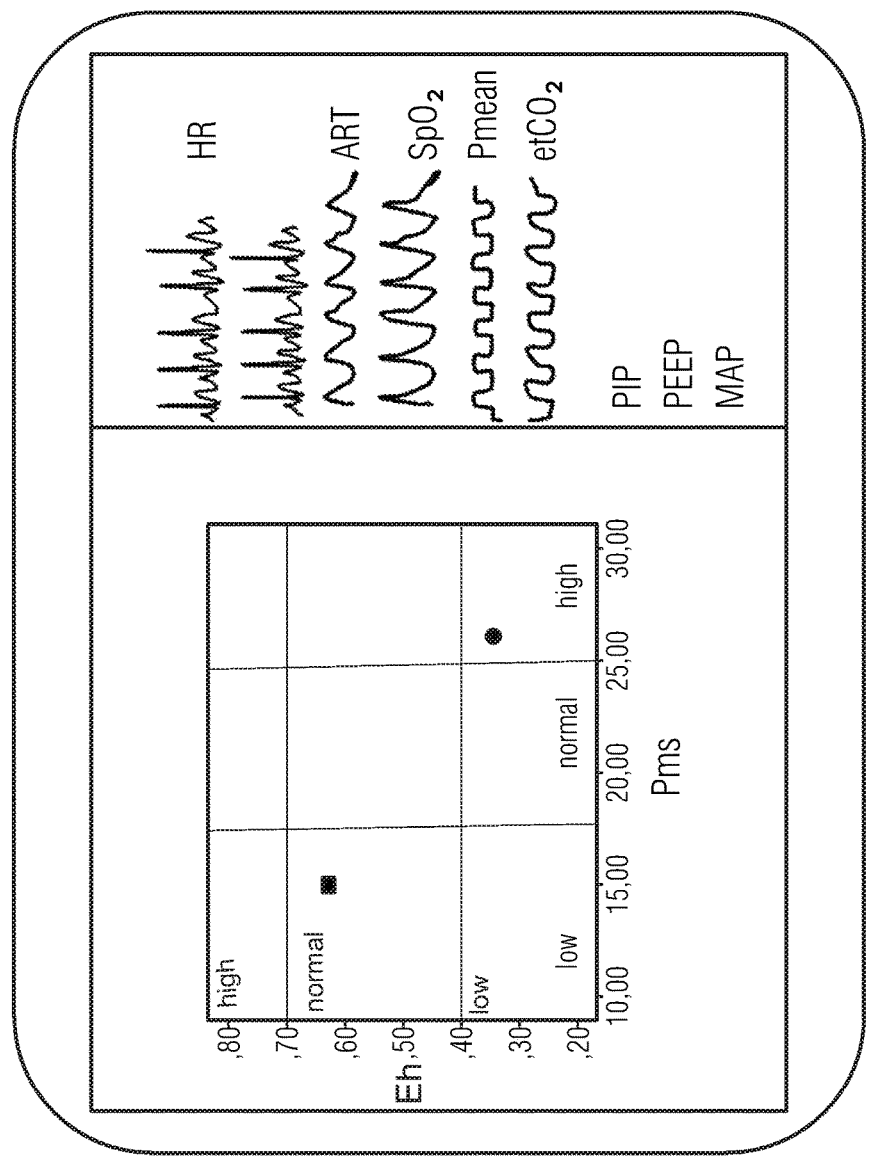
FIG. 1 is a schematic view of the display of a display device of a monitoring device according to the present invention for the state display for a patient.

FIG. 1 shows a schematic view of the display of a display device, in which the state variables are shown without pressure correction (round mark) and the pressure-corrected state variables (square mark) as points in a Cartesian system of coordinates comprising the cardiac efficiency Eh and the mean systemic filling pressure Pms. This example shows that a markedly different evaluation results from the previous derivation and display (without pressure correction). After deriving the pressure-corrected state variables, the result is obtained that the mean systemic filling pressure is actually too low and the cardiac efficiency is actually good, which produces the exact opposite of the evaluation of the state variables without pressure correction and which requires other countermeasures. The evaluation with the pressure-corrected state variables Pms and Eh is actually very much closer to reality and also corresponded to the evaluation of the clinician and is consistent with other measured hemodynamic parameters (good heartbeat performance, normal blood pressure, high performance of ejection, low RAP under PEEP) such that a markedly improved recording of the state of circulation due to the corrected state variables $Pms_p$ and $Eh_p$ is assumed.

In another example, the circulation of a patient with the following data was monitored:
Patient: Male, 72 years old, 180 cm, 103 kg (overweight), acute lung failure after massive transfusion;
cardiac index 4.2 L/min./m2, heart rate 86 per min., blood pressure 131/51 mmHg (MAP 71 mmHg), RAP 14 mmHg;
assisted spontaneous breathing with a PEEP of 12 mbar.

Without taking the pressure assistance into consideration, the following values are obtained for the mean systemic filling pressure Pms and the cardiac efficiency Eh from the right atrial pressure RAP, the mean arterial pressure MAP and the cardiac output CO:
Pms=21.81 (clinical evaluation: adequate)
Eh=0.39 (clinical evaluation: low).

By carrying out the pressure correction, the following pressure-corrected state variables are obtained again in this example with the formulas [3] and [4]:
$Pms_p$=13.05 (clinical evaluation: too low)
$Eh_p$=0.63 (clinical evaluation: good).

Figure 2:
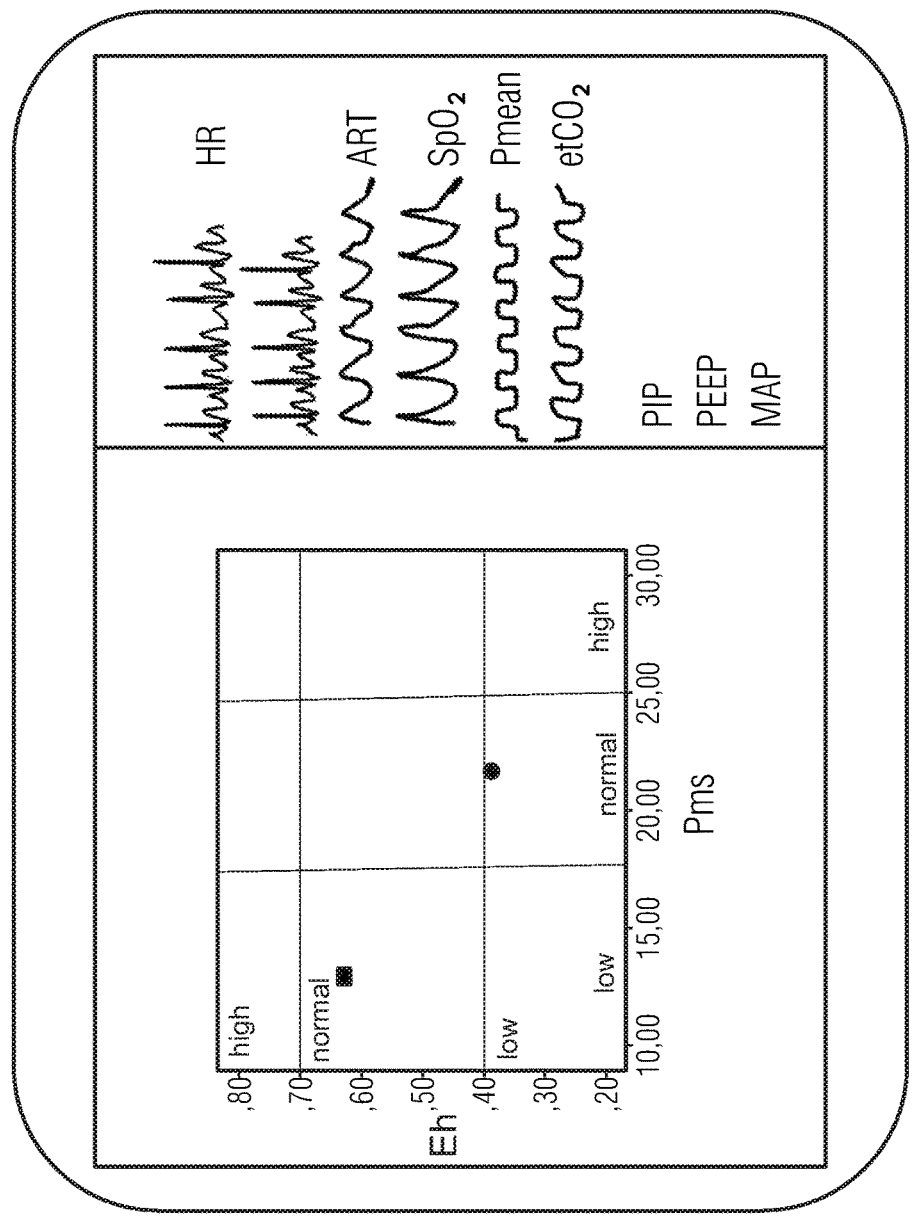
FIG. 2 is a schematic view showing a second example of a state display for another patient.

The graphic representation of these state variables is shown in FIG. 2 in a Cartesian system of coordinates with the cardiac efficiency on the Y axis and the mean systemic filling pressure on the X axis, and the derived values of the state variables after conventional determination are shown with a round symbol and the state variables determined according to the present invention with pressure correction are shown with a square symbol. It is also shown here that after taking into consideration the pressure correction, a markedly different evaluation of the state of the circulation of the patient is made: Without pressure correction, the mean systemic filling pressure Pms would be evaluated as adequate and the cardiac efficiency Eh as too low, whereas after taking the pressure correction into consideration, a markedly different evaluation of the state of the circulation of the patient is obtained, namely a pressure-corrected mean systemic filling pressure, which is evaluated as too low, and a pressure-corrected cardiac efficiency $Eh_p$, which is evaluated as good. This evaluation after pressure correction also corresponded to the evaluation of the clinician and is consistent with the other measured hemodynamic parameters (good heartbeat performance, normal blood pressure, high ejection performance, low RAP under PEEP).

It is consequently shown that a markedly more reliable recording of the state of the circulatory system of positive-pressure-ventilated patients is achieved with the monitoring device according to the present invention compared to the state of the art.

While specific embodiments of the invention have been shown and described in detail to illustrate the application of the principles of the invention, it will be understood that the invention may be embodied otherwise without departing from such principles.

The invention claimed is:

1. A monitoring device for monitoring a state of circulation of a patient ventilated with positive-pressure ventilation, the monitoring device comprising:
   a data recording and analysis device receiving patient circulation data comprising a determined right atrial pressure, a mean arterial pressure and a cardiac output characterizing a current state of circulation of the patient, and further receiving a person-specific data factor and a pressure value characterizing a pressure assistance during the positive-pressure ventilation, wherein:
   the data recording and analysis device is configured to determine a mean systemic filling pressure value as a function of the right atrial pressure, the mean arterial pressure, the person-specific data factor and the cardiac output;

the data recording and analysis device is configured to determine a cardiac efficiency value as a function of the mean systemic filling pressure and the right atrial pressure with predetermined factors and the person-specific data factor;

the data recording and analysis device is configured to determine a pressure-corrected mean systemic filling pressure value as a function of: a difference between the right atrial pressure and the pressure value characterizing a pressure assistance during the positive-pressure ventilation, the mean arterial pressure, the person-specific data factor, and the cardiac output; and the data recording and analysis device is configured to determine a pressure-corrected cardiac efficiency value as a function of: the difference between the right atrial pressure and the pressure value characterizing the pressure assistance during the positive-pressure ventilation, the mean arterial pressure, the person-specific data factor, and the cardiac output; and a display connected to the data recording and analysis device and displaying the mean systemic filling pressure value and the cardiac efficiency value, in a system of coordinates on the display and displaying the pressure-corrected mean systemic filling pressure value and the pressure-corrected cardiac efficiency value in the system of coordinates on the display, wherein:

the data recording and analysis device is configured to determine the pressure-corrected mean systemic pressure ($Pms_p$) based on an equation as follows:

$$Pms_p = a \cdot (RAP - K \cdot Pps,char) + b \cdot MAP + c \cdot CO$$

in which:
RAP: is the right atrial pressure (mmHg)
K: is a pressure conversion factor
MAP: is the mean arterial pressure (mmHg)
CO: is the cardiac output (L/min)
Pps,char: is the pressure value characterizing the pressure assistance during the positive-pressure ventilation (mbar)
a: is a predetermined factor (dimensionless) of the predetermined factors
b: is a predetermined factor (dimensionless) of the predetermined factors
c: is the person-specific factor (dyn·sec·cm$^{-5}$·m$^2$); and
the data recording and analysis device is configured to determine the pressure-corrected cardiac efficiency ($Eh_p$) based on an equation as follows:

$$Eh_p = \frac{Pms_p - (RAP - K \cdot Pps, char)}{Pms_p}.$$

2. A monitoring device in accordance with claim 1, wherein the pressure conversion factor K is equal to 0.76 for unit conversion of a mbar value of Pps,char to the units mmHg of RAP.

3. A method for monitoring a state of circulation of a patient ventilated with positive-pressure ventilation, the method comprising the steps of:
receiving and storing data characterizing a current state of circulation of the patient;
receiving and storing person-specific data;
determining a right atrial pressure, a mean arterial pressure and a cardiac output from the data characterizing the current state of circulation of the patient;

determining a mean systemic filling pressure from the right atrial pressure, the mean arterial pressure and the cardiac output;
determining a cardiac efficiency from the mean systemic filling pressure and from the right atrial pressure by means of linear combination with predetermined factors and with factors dependent on the person-specific data;
displaying the determined mean systemic filling pressure and the cardiac efficiency as a current state in a system of coordinates defined by the cardiac efficiency and the mean systemic filling pressure on a display device; and
determining a pressure-corrected mean systemic filling pressure as a function of a difference from the right atrial pressure and a pressure value characterizing a pressure assistance during the positive-pressure ventilation;
determining a pressure-corrected cardiac efficiency as a function of the difference from the right atrial pressure and the pressure value characterizing the pressure assistance during the positive-pressure ventilation; and
displaying the pressure-corrected mean systemic filling pressure and the pressure-corrected cardiac efficiency in the system of coordinates on the display, wherein:
the pressure-corrected mean systemic pressure ($Pms_p$) is determined based on an equation as follows:

$$Pms_p = a \cdot (RAP - K \cdot Pps, char) + b \cdot MAP + c \cdot CO$$

in which:
RAP: is the right atrial pressure (mmHg)
K: is a pressure conversion factor
MAP: is the mean arterial pressure (mmHg)
CO: is the cardiac output (L/min)
Pps,char: is the pressure value characterizing the pressure assistance during the positive-pressure ventilation (mbar)
a: is a predetermined factor (dimensionless) of the predetermined factors
b: is a predetermined factor (dimensionless) of the predetermined factors
c: is the person-specific factor (dyn·sec·cm$^{-5}$·m$^2$); and
the pressure-corrected cardiac efficiency ($Eh_p$) is determined based on an equation as follows:

$$Eh_p = \frac{[a \cdot (RAP - K \cdot Pps, char) + b \cdot MAP + c \cdot CO] - [RAP - K \cdot Pps, char]}{a \cdot (RAP - K \cdot Pps, char) + b \cdot MAP + c \cdot CO}.$$

4. A method in accordance with claim 3, wherein:
the pressure conversion factor K is equal to 0.76 for unit conversion of a mbar value of Pps,char to the units mmHg of RAP; and
the steps of the method are executed with a computer program product configured to control a data recording and analysis device with said computer program product being run on said data recording and analysis device in order to receive a positive end-expiratory pressure as the pressure value characterizing the pressure assistance.

5. A method in accordance with claim 3 wherein a positive end-expiratory pressure is used as the pressure value characterizing the pressure assistance during positive-pressure ventilation.

6. A method in accordance with claim 3, further comprising:

storing states of pressure-corrected mean systemic filling pressure and pressure-corrected cardiac efficiency as a function of time; and displaying a current state from the pressure-corrected mean systemic filling pressure and the pressure-corrected cardiac efficiency together with the stored states at past points in time in the system of coordinates whereby a course of development of the state is shown on the display.

7. A method in accordance with claim 6, wherein the course of development is displayed as a state curve or trajectory with a time stamp along the state curve in the system of coordinates.

8. A monitoring device for monitoring a state of circulation of a patient ventilated with positive-pressure ventilation, the monitoring device comprising a data recording and analysis device with received patient circulation data characterizing a current state of circulation of the patient, the received patient circulation data comprising a right atrial pressure, a mean arterial pressure, a cardiac output, a person-specific data factor, and a pressure value characterizing a pressure assistance during the positive-pressure ventilation, wherein the data recording and analysis device is configured to:

determine a pressure-corrected mean systemic filling pressure value as a function of: a difference between the right atrial pressure and the pressure value characterizing a pressure assistance during the positive-pressure ventilation, the mean arterial pressure, the person-specific data factor, and the cardiac output, wherein the data recording and analysis device is configured to determine the pressure-corrected mean systemic pressure ($Pms_p$) based on an equation as follows:

$$Pms_p = a \cdot (RAP - K \cdot Pps,char) + b \cdot MAP + c \cdot CO$$

in which:
RAP: is the right atrial pressure
K: is a pressure conversion factor
MAP: is the mean arterial pressure
CO: is the cardiac output
Pps,char: is the pressure value characterizing the pressure assistance during the positive-pressure ventilation a: is a predetermined factor of the predetermined factors
b: is a predetermined factor of the predetermined factors
c: is the person-specific factor; and determine a pressure-corrected cardiac efficiency value ($Eh_p$) based on subtracting a value based on RAP from the determined pressure-corrected mean systemic pressure ($Pms_p$) to form a difference and dividing the difference by the determined pressure-corrected mean systemic pressure ($Pms_p$); and a display connected to the data recording and analysis device and displaying the pressure-corrected mean systemic filling pressure value and the pressure-corrected cardiac efficiency value in a cardiac efficiency and mean systemic filling pressure system of coordinates.

9. A monitoring device in accordance with claim 8, wherein the pressure conversion factor K is equal to 0.76 for unit conversion of a mbar value of Pps,char to the units mmHg of RAP.

10. A monitoring device in accordance with claim 8, wherein:

the data recording and analysis device is configured to determine a mean systemic filling pressure value as a function of the right atrial pressure, the mean arterial pressure, the person-specific data factor and the cardiac output;

the data recording and analysis device is configured to determine a cardiac efficiency value as a function of the mean arterial pressure, the right atrial pressure, the person-specific data factor and the cardiac output; and the display displays the mean systemic filling pressure value and the cardiac efficiency value simultaneously with the display of the pressure-corrected mean systemic filling pressure value and the pressure-corrected cardiac efficiency value.

11. A monitoring device in accordance with claim 8, wherein the pressure value characterizing the pressure assistance during the positive-pressure ventilation is a positive end-expiratory pressure of the patient ventilated with positive-pressure ventilation and the pressure conversion factor K is equal to 0.76 for unit conversion of a mbar value of Pps,char to the units mmHg of RAP.

* * * * *